US007598388B2

(12) United States Patent
Tsai et al.

(10) Patent No.: US 7,598,388 B2
(45) Date of Patent: Oct. 6, 2009

(54) CARBENE CONTAINING METAL COMPLEXES AS OLEDS

(75) Inventors: Jui-Yi Tsai, Monroeville, PA (US);
Michael S. Barone, Pittsburgh, PA (US);
Arnold Tamayo, Glendale, CA (US);
Mark E. Thompson, Anaheim Hills, CA (US)

(73) Assignees: The University of Southern California, Los Angeles, CA (US); Universal Display Corporation, Ewing, NJ (US)

( * ) Notice: Subject to any disclaimer, the term of this patent is extended or adjusted under 35 U.S.C. 154(b) by 637 days.

(21) Appl. No.: 11/032,739

(22) Filed: Jan. 10, 2005

(65) Prior Publication Data

US 2005/0258742 A1  Nov. 24, 2005

Related U.S. Application Data

(63) Continuation-in-part of application No. 10/880,384, filed on Jun. 28, 2004, which is a continuation-in-part of application No. 10/849,301, filed on May 18, 2004.

(51) Int. Cl.
*C07F 15/00* (2006.01)
(52) U.S. Cl. .......................... 548/103; 313/504; 546/2; 548/101
(58) Field of Classification Search ................ 548/101, 548/103; 546/2; 313/504
See application file for complete search history.

(56) References Cited

U.S. PATENT DOCUMENTS

| | | | |
|---|---|---|---|
| 4,769,292 A | 9/1988 | Tang et al. | |
| 5,247,190 A | 9/1993 | Friend et al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,160,267 A * | 12/2000 | Kunugi et al. | 257/40 |
| 6,294,398 B1 | 9/2001 | Kim et al. | |
| 6,303,238 B1 | 10/2001 | Thompson et al. | |
| 6,310,360 B1 | 10/2001 | Forrest et al. | |
| 6,337,102 B1 | 1/2002 | Forrest et al. | |
| 6,383,666 B1 | 5/2002 | Kim et al. | |
| 6,420,057 B1 | 7/2002 | Ueda et al. | |
| 6,458,475 B1 | 10/2002 | Adachi | |
| 6,468,819 B1 | 10/2002 | Kim et al. | |

(Continued)

FOREIGN PATENT DOCUMENTS

| | | |
|---|---|---|
| EP | 1 191 613 | 3/2002 |
| EP | 1 191 614 | 3/2002 |
| EP | 1 239 526 | 9/2002 |

(Continued)

OTHER PUBLICATIONS

Son et al., "Synthesis of Ru(II) Complexes of N-Heterocyclic Carbenes and Their Promising Photoluminescence Properties in Water", Iorg. Chem., vol. XX, No. XX, pp. A-C.

(Continued)

*Primary Examiner*—Porfirio Nazario Gonzalez
(74) *Attorney, Agent, or Firm*—Kenyon & Kenyon LLP

(57) ABSTRACT

A process for preparing a compound having the formula $L_2IrL'$ is provided. The process comprises:
combining

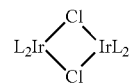

and L' in the presence of an organic solvent to form a mixture, wherein L is a suitable carbene ligand precursor coordinated to Ir; and L' is a bidentate ligand or two monodentate ligands, and L is different from L';
Also provided is a process for preparing a compound having the formula

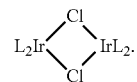

The process comprises:
(a) combining L, a carbene ligand precursor, with an organic solvent;
(b) maintaining the mixture of step (a) at a temperature from about 175° C. to less than the boiling point of the organic solvent in (a).
A process for preparing a compound with the formula $L_3Ir$ is also provided. This process comprises combining

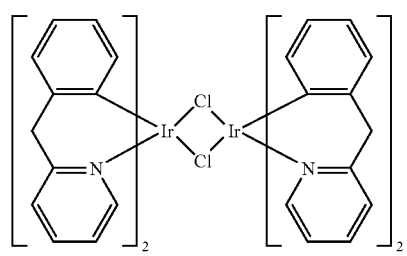

and L in the presence of alcohol and a base to form a mixture, wherein L is a bidentate ligand that may form a five-membered chelate ring.

4 Claims, 2 Drawing Sheets

U.S. PATENT DOCUMENTS

| | | | |
|---|---|---|---|
| 6,548,956 | B2 | 4/2003 | Forrest et al. |
| 6,576,134 | B1 | 6/2003 | Agner |
| 6,602,540 | B2 | 8/2003 | Gu et al. |
| 2001/0015432 | A1 | 8/2001 | Igarashi |
| 2001/0019782 | A1 | 9/2001 | Igarashi et al. |
| 2002/0024293 | A1 | 2/2002 | Igarashi et al. |
| 2002/0034656 | A1 | 3/2002 | Thompson et al. |
| 2002/0048689 | A1 | 4/2002 | Igarashi et al. |
| 2002/0063516 | A1 | 5/2002 | Tsuboyama et al. |
| 2002/0064681 | A1 | 5/2002 | Takiguchi et al. |
| 2002/0071963 | A1 | 6/2002 | Fujii |
| 2002/0121638 | A1 | 9/2002 | Grushin et al. |
| 2002/0182441 | A1 | 12/2002 | Lamansky et al. |
| 2002/0190250 | A1 | 12/2002 | Grushin et al. |
| 2003/0068526 | A1 | 4/2003 | Kamatani et al. |
| 2003/0068536 | A1 | 4/2003 | Tsuboyama et al. |
| 2003/0072964 | A1 | 4/2003 | Kwong et al. |
| 2003/0091862 | A1 | 5/2003 | Tokito et al. |
| 2003/0096138 | A1 | 5/2003 | Lecloux et al. |
| 2003/0141809 | A1 | 7/2003 | Furugori et al. |
| 2003/0162299 | A1 | 8/2003 | Hsieh et al. |
| 2003/0230980 | A1 | 12/2003 | Forrest et al. |
| 2004/0075096 | A1 | 4/2004 | Grushin et al. ............. 257/79 |
| 2004/0174116 | A1 | 9/2004 | Lu et al. |
| 2005/0230665 | A1* | 10/2005 | Thompson ............. 252/500 |
| 2005/0260448 | A1* | 11/2005 | Lin et al. ............. 428/690 |
| 2006/0258043 | A1 | 11/2006 | Bold |
| 2008/0018221 | A1* | 1/2008 | Egen et al. ............. 313/483 |
| 2008/0200686 | A1* | 8/2008 | Molt et al. ............. 548/103 |

FOREIGN PATENT DOCUMENTS

| | | |
|---|---|---|
| WO | WO 92/02714 | 2/1992 |
| WO | WO 02/02714 | 1/2002 |
| WO | WO 02/15645 | 2/2002 |
| WO | WO 02/074015 | 9/2002 |
| WO | WO 03/084972 | 10/2003 |
| WO | WO 03/088271 | 10/2003 |
| WO | WO 03/099959 | 12/2003 |

OTHER PUBLICATIONS

Baldo et al., "Highly Efficient Phosphorescent Emission from Organic Electroluminescent Devices," Nature, vol. 395, pp. 151-154 (1998).

Baldo et al., "Very High-Efficiency Green Organic Light-Emitting Devices Based on Electrophosphorescence," Appl. Phys. Lett., vol. 75, No. 3, pp. 4-6 (1999).

Adachi et al., "Nearly 100% Internal Phosphorescent Efficiency in an Organic Light Emmitting Device," J. Appl. Phys., vol. 90, pp. 5048-05051 (2001).

"Inorganic Chemistry" (2$^{nd}$ Edition) by Gary L. Miessler and Donald A. Tarr, Prentice Hall, pp. 1-3, 422-424, 442, Aug. 1999 version.

Thomas H. Lowry et al., "Mechanism and Theory in Organic Chemistry," Harper & Row Publishers, New York, p. 256 (1976).

Nicholas J. Turro, Modern Molecular Photochemistry, University Science Books, Sausalito, California, pp. 109-110.

Nemcsok et al., "The Significance of π Interactions in Group 11 Complexes with N-Heterocyclic Carbenes", Organometallics, vol. 23, pp. 3640-3646, 2004.

Koizumi et al., "Terpyridine-Analogous (N,N,C)-Tridentate Ligands: Synthesis, Structures, and Electrochemical Properties of Ruthenium (II) Complexes Bearing Gtridentate Pyridinium and Pyridinylidene Ligands," Organometallics, vol. 22, pp. 970-975 (2003).

Bourissou et al., "Stable Carbenes," Chem Rev. vol. 100, pp. 39-91 (2000).

Ashekenazi et al., "Discovery of the First Metallaquinone," J. Am. Chem. Soc., vol. 122, pp. 8797-8798 (2000).

Cattoën, et al., "Amino-Aryl-Carbenes: Alternative Ligands for Transition Metals?" J. Am. Chem. Soc., vol. 126, pp. 1342-1343 (2004).

Wong et al., "Ruthenium (II) o-Acetylide and Carbene Complexes Supported by the Terpyridine-Bipyridine Ligand Set: Structural, Spectroscopic, and Photochemical Studies," Organometallics, vol. 23, pp. 2263-2272 (2004).

Klapars et al., "A General and Efficient Copper Catalyst for the Amidation of Aryl Halides and the N-Arylation of Nitrogen Heterocycles," J. Am. Chem. Soc., vol. 123, pp. 7727-7729 (2001).

Lai et al., "Carbene andf Isocyanide Ligation at Luminescent Cyclometalated 6-Phenyl-2,2'-bipyridyl Platinum (II) Complexes: Structural and Spectroscopic Studies," Organometallics, vol. 18, pp. 3327-3336 (1999).

Xue et al., "Spectroscopic and Excited-State Properties of Luminescent Rhenium (I) N-Heterocyclic Carbene Complexes Containing Aromatic Diimine Ligands," Organometallics, vol. 17, pp. 1622-1630 (1998).

Wang et al., "Facile Synthesis of Silver (I)-Carbene Complexes. Useful Carbene Transfer Agents," Organometallics, vol. 17, pp. 972-975 (1998).

Cardin et al., "Transition Metal-Carbene Complexes," Chem. Rev., vol. 72, pp. 545-574 (1972).

Kunkley et al., "Optical Properties of Transition Metal Complexes with N-Heterocyclic Carbenes as Ligands. 1,3-di-t-Butylimidazol-2-ylidene as Charge Transfer Donor and Acceptor," J. Organomettalic Chem., vol. 684, pp. 113-116 (2003).

Anthony R. Chianese et al., "Abnormal C5-Bound N-Heterocyclic Carbenes: Extremely Strong Electron Donor Ligands and Their Iridium (I) and Iridium (III) Complexes," Organometallics, vol. 23, pp. 2461-2468 (2004).

Xile Hu et al., "Group 11 Metal Complexes of N-Heterocyclic Carbene Ligands: Nature of the Metal-Carbene Bone," Organometallics, vol. 23, pp. 755-764 (2004).

Xile Hu et al., "A Bis-Carbenealkenyl Copper(I) Complex from a Tripodal Tris-Carbene Ligand," Organometallics, vol. 22, pp. 3016-3018 (2003).

Siu-Wai Lai et al., "[{Pt(CN)($C_{10}H_{21}N_4$)}$_6$]: A Luminescent Hexanuclear Platinum (II) Macrocycle Containing Chelating Dicarbene and Bridging Cyanide Ligands," Angnew. Chem. Int. Ed., vol. 37, No. 1/2, pp. 182-184 (1998).

Xile Hu et al., "Silver Complexes of a Novel Tripodal N-Heterocyclic Carbene Ligand: Evidence for Significant Metal-Carbene π-Interaction," Organometallics, vol. 22, pp. 612-614 (2003).

James P. Collman et al., "Principles and Applications of Organotransition Metal Chemistry," University Science Books, Mill Valley, CA, pp. 119-121 (1987).

Nicholas A. Piro, et al., "Pyridinium-derived N-heterocyclic carbene ligands: syntheses, structures and reactivity of N-(2'-pyridyl)pyridin-2-ylidene complexes of nickel(II), palladium(II) and platinum(KK)", Polyhedron 23 (2004), pp. 2797-2804.

Take-aki Koizumi, et al., "Synthesis and electrochemical properties of bis(bipyridine)ruthenium(II) complexes bearing pyridinyl- and pyridinylidene ligands induced by cyclometalation of N'-methylated bipyridium analogs", Journal of Organometallic Chemistry, vol. 690, Issue 5, Mar. 1, 2005, pp. 1258-1264.

S. Lamansky, et al., "Highly Phosphorescent Bis-Cyclometalated Iridium Complexes: Synthesis, Photophysical Characterization, and Use in Organic Light Emitting Diodes", *J. Am. Chem. Soc.*, 2001, 123, pp. 4304-4312.

R.J. Holmes, et al., "Efficient, deep-blue organic electrophosphorescence by guest charge trapping", *Applied Physics Letters*, vol. 83, No. 18, pp. 3618-3818, Nov. 3, 2003.

U.S. Appl. No. 10/233,470, to Shtein et al., filed Sep. 4, 2002.

U.S. Appl. No. 10/680,066, to Ren et al., filed Oct. 6, 2003.

U.S. Appl. No. 10/771,423, filed Feb. 3, 2004, to Ma et al.

Hitchcock et al., Synthesis of Homoleptic Tris(Organo-Chelate)Iridium(III) Complexes By Spontaneous ortho-Metallation of Electron-Rich Olefin-Derived N,N'Diarylcarbene Ligands and The X-Ray Structures of Fac-[Ir{CN($C_6H_4$Me-p)($CH_2$)$_2$N$C_6H_3$Me-p}3 and mer-[Ir-{CN($C_6H_4$-Me-p)($CH_2$)$_2$N$C_6H_3$Me-p}2 {CN($C_6H_4$Me-p)($CH_2$)$_2$N$C_6H_4$Me-p}](A Product of of HCl Cleavage), J. of Organometallic Chemistry, 239(1982); C26-C30.

Grundemann et al., Abnormal Ligand Binding and Reversible Ring Hydrogenation in the Reaction of Imidazolium Salts with Ir$H_5$(P$Ph_3$)$_2$.

* cited by examiner

CARBENE CONTAINING METAL COMPLEXES AS OLEDS

This application is a continuation-in-part of U.S. application Ser. No. 10/880,384, filed Jun. 28, 2004, entitled Luminescent Compounds with Carbene Ligands, which is a continuation-in-part of U.S. application Ser. No. 10/849,301, filed May 18, 2004, and both of which are incorporated by reference in its entirety.

JOINT RESEARCH AGREEMENT

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices (OLEDs), and more specifically to processes for preparing phosphorescent organic materials used in such devices. More specifically, the present invention relates to processes for preparing carbene-metal complexes incorporated into OLEDs.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

The carbene ligand has been well known in organometallic chemistry, and is used to generate a wide range of thermally stable catalytic materials. The carbene ligands have been employed both as active groups, directly engaged in the catalytic reactions, and serving a role of stabilizing the metal in a particular oxidation state or coordination geometry. However, applications of carbene ligands are not well known in photochemistry.

One issue with many existing organic electroluminescent compounds is that they are not sufficiently stable for use in commercial devices. An object of the invention is to provide a class of organic emissive compounds having improved stability.

In addition, existing compounds do not include compounds that are stable emitters for high energy spectra, such as a blue spectra. An object of the invention is to provide a class of organic emissive compounds that can emit light with various spectra, including high energy spectra such as blue, in a stable manner.

SUMMARY OF THE INVENTION

In one aspect, a process for preparing a compound having the formula $L_2IrL'$ is provided. The process comprises:
(a) combining

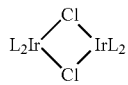

and L' in the presence of an organic solvent to form a mixture, wherein L is a carbene ligand coordinated to Ir; and L' is a bidentate ligand or two monodentate ligands, and L is different from L';
(b) maintaining the mixture for sufficient time to obtain $L_2IrL'$;
(c) recovering $L_2IrL'$ from the mixture.

In another aspect, a process for preparing a compound having the formula

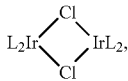

is provided. The process comprises:
(a) combining L with an organic solvent, wherein L is a suitable carbene ligand precursor;
(b) maintaining the mixture of step (a) at a temperature from about 175° C. to less than the boiling point of the organic solvent in (a) to obtain

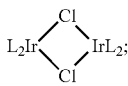

and
(c) recovering

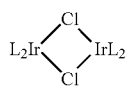

from the mixture.

A process for preparing a compound with the formula $L_3Ir$ is also provided in another aspect. This process comprises:
(a) combining

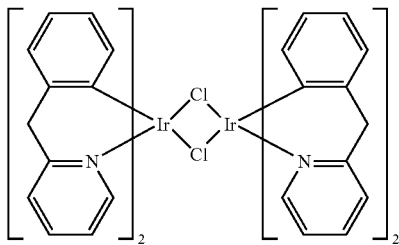

and L in the presence of alcohol and a base to form a mixture, wherein L is a bidentate ligand that may form a five-membered chelate ring;
(b) maintaining the mixture for sufficient time to obtain $L_3Ir$; and
(c) recovering $L_3Ir$ from the mixture.

Compounds prepared from these processes may be incorporated into OLEDs.

DETAILED DESCRIPTION

Figure 1:
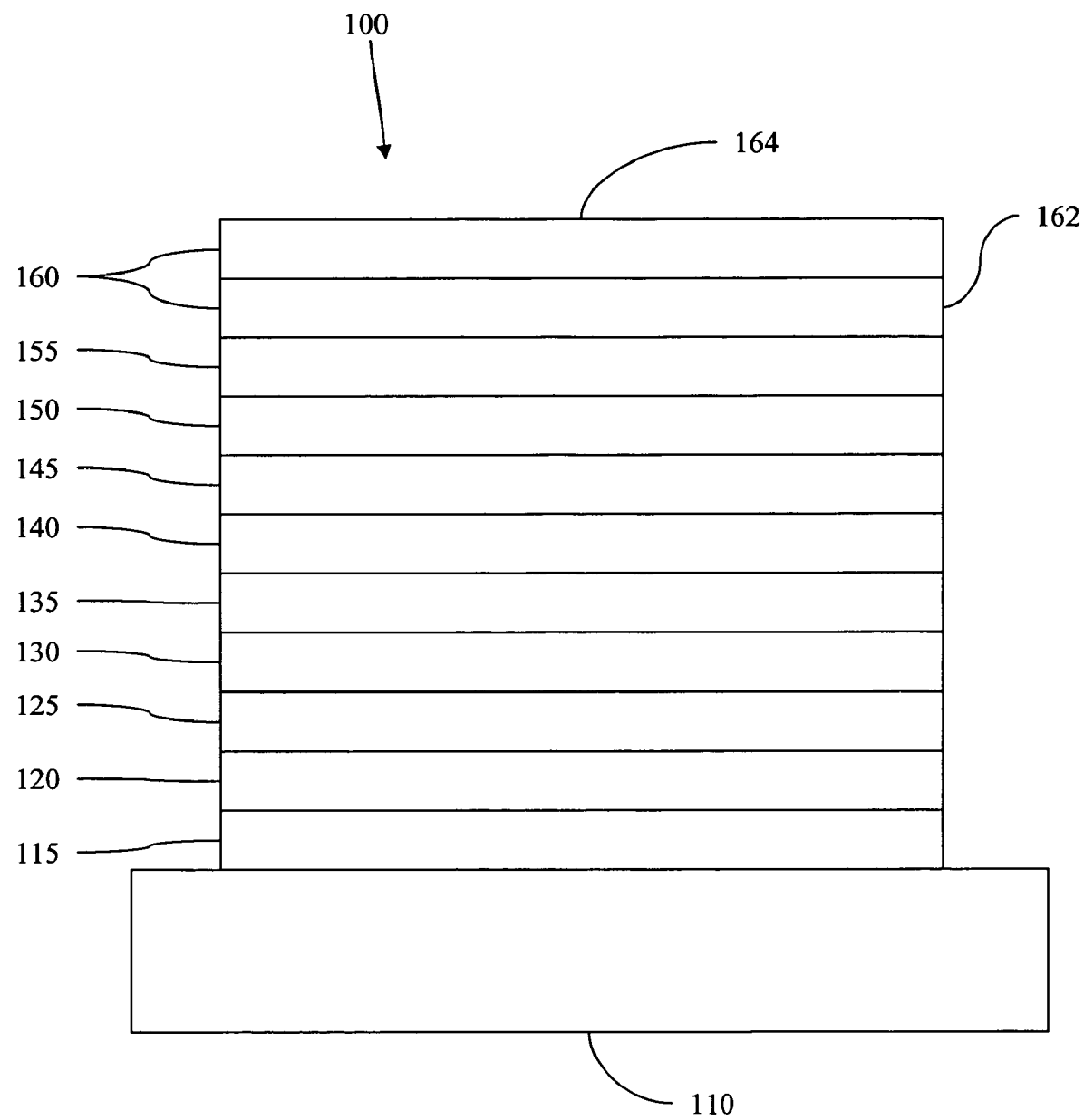
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organo-metallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

The term "organometallic" as used herein is as generally understood by one of ordinary skill in the art and as given, for example, in "Inorganic Chemistry" (2nd Edition) by Gary L. Miessler and Donald A. Tarr, Prentice-Hall (1998). Thus, the term organometallic refers to compounds which have an organic group bonded to a metal through a carbon-metal bond. This class does not include per se coordination compounds, which are substances having only donor bonds from heteroatoms, such as metal complexes of amines, halides, pseudohalides (CN, etc.), and the like. In practice organometallic compounds generally comprise, in addition to one or more carbon-metal bonds to an organic species, one or more donor bonds from a heteroatom. The carbon-metal bond to an organic species refers to a direct bond between a metal and a carbon atom of an organic group, such as phenyl, alkyl, alkenyl, etc., but does not refer to a metal bond to an "inorganic carbon," such as the carbon of CN or CO.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the luminescent properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels directly involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2, and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, as would be understood by one of skill in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
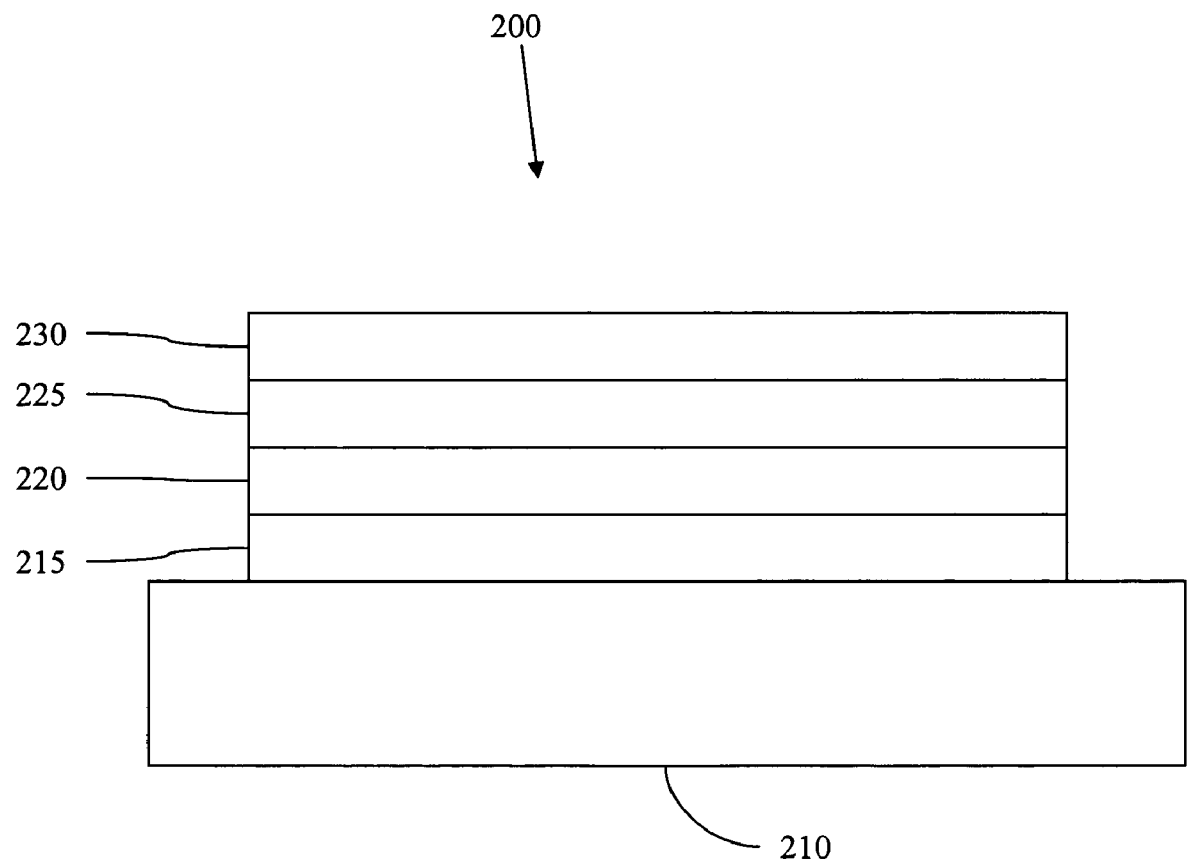
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

A process for preparing compounds comprising a carbene ligand bound to a metal center is provided. Carbene compounds include small molecules, dendrimers, and polymers that include a carbene-metal bond. In one embodiment, the compound is a phosphorescent emissive material, preferably a dopant. The compound may also be doped into a wide band gap host material such as disclosed in U.S. patent application Ser. No. 10/680,066, which is incorporated by reference in its entirety, or it may be doped into an inert wide band gap host such as disclosed in WO-074015, which is incorporated by reference in its entirety.

In another embodiment, the metal-carbene compound is a host material in an emissive layer. For example, the metal-carbene compound may be used as a high energy host materials for doped blue devices. The dopant in this case could be a triplet emitter or a singlet emitter (using phosphor sensitized fluorescence). In some embodiments, the dopant is a blue or UV emissive material. In this case, the host material preferably has a wide energy gap. As used herein, the energy gap refers to the difference in the energy between the highest occupied molecular orbital (HOMO) and the lowest unoccupied molecular orbital (LUMO) for a particular compound. The triplet energy for a given material is related to, but less than, the energy gap. Materials for use as a wide gap host are selected to have a wide energy gap so that the host material does not quench the dopant emission by endothermic or exothermic energy transfer. The wide gap host is preferably selected so as to have a triplet energy at least about 300 mV higher than that of the dopant.

Additionally, the high band gap of metal-carbene compounds may make these materials effective in carrier blocking and transporting layers. Specifically, these materials may be used in the electron blocking layer, hole blocking layer, exciton blocking layer, hole transport layer, or electron transport layer of an OLED. In other embodiments a metal-carbene compound may be used as a hole injection layer, electron injection layer, or protective layer. It is believed that metal-carbene compounds described herein have improved thermal stability when incorporated into an organic light emitting device due to the carbene-metal bond, as compared to existing compounds without a carbene-metal bond.

As used herein, the term "carbene" refers to compounds having a divalent carbon atom with only six electrons in its valence shell when not coordinated to a metal. A useful exercise to determine whether a ligand includes a carbene-metal bond is to mentally deconstruct the complex as a metal fragment and a ligand, and to then determine whether a carbon atom in the ligand that was previously bound to the metal is a neutral divalent carbon atom in the deconstructed state. The resonance forms of a preferred embodiment may be shown as:

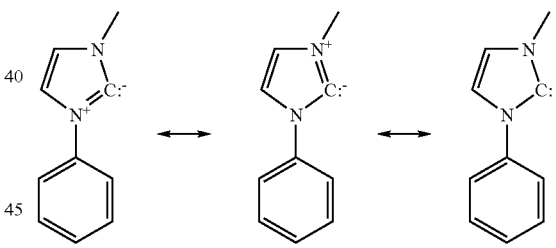

This definition of carbene is not limited to metal-carbene complexes synthesized from carbenes, but is rather intended to address the orbital structure and electron distribution associated with the carbon atom that is bound to the metal. The definition recognizes that the "carbene" may not technically be divalent when bound to the metal, but it would be divalent if it were detached from the metal. Although many such compounds are synthesized by first synthesizing a carbene and then binding it to a metal, the definition is intended to encompass compounds synthesized by other methods that have a similar orbital structure and electron configuration. Lowry & Richardson, *Mechanism and Theory in Organic Chemistry* 256 (Harper & Row, 1976) defines "carbene" in a way that is consistent with the way the term is used herein. Some references may define "carbene" as a carbon ligand that forms a double bond to a metal. While this definition is not being used in the present application, there may be some overlap between the two definitions. A variety of representations are used to depict the bonding in such carbenes, including those in which a curved line is used to indicate partial multiple bonding between the carbene carbon and the adjacent heteroatom(s).

In the figures and structures herein, a carbene-metal bond may be depicted as C→M, as for example:

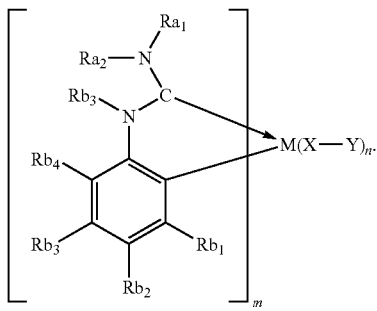

Such structures that use an arrow to represent the presence of a metal-carbene bond are used intercahngeably herein with structures that do not include the arrow, without any intention of suggesting there is a difference in the structure shown.

Carbene ligands are especially desirable in OLED applications due to the high thermal stability exhibited by metal-carbene complexes. It is believed that the carbene, which behaves much as an electron donative group, generally bonds strongly to the metals, thus forming a more thermally stable complex than, for example, previous cyclometallated complexes used as phosphorescent emitters. It is also believed that carbene analogs of ligands employed in existing phosphorescent emissive materials (for example the phenylpyridine or Irppy, etc.) may exhibit greater stability and emit at substantially higher energy than their existing analogs.

As used herein, a "non-carbene analog" of a metal carbene compound refers to existing ligands having a substantially similar chemical structure to the metal-carbene compound, but unlike the carbene compounds of the present invention, which features a carbene-metal bond, the analog has some other bond, such as a carbon-metal or a nitrogen-metal bond, in place of the carbene-metal bond. For example, Ir(ppz)$_3$ has a nitrogen in each ligand bound to the Ir. Ir(1-phenylimidazolin-2-ylidene) is analogous to Ir(ppz)$_3$ where the nitrogen bound to the Ir has been replaced with a carbene bound to the Ir, and where the atoms surrounding the carbene have been changed to make the carbon a carbene. Thus, embodiments of the present invention include metal-carbene complexes (e.g. Ir(1-phenylimidazolin-2-ylidene) with similar structures to existing emissive compounds (e.g. Ir(ppz)$_3$).

Examples of existing emissive compounds include Ir(ppy)$_3$ and Ir(ppz)$_3$, discussed above. Other examples are disclosed in the references below, which are incorporated herein by reference in their entirety. In preferred embodiments, the carbene ligands are imidazoles, pyrazoles, benzimidazoles, and pyrroles.

It is believed that the carbene-metal bond in Ir(1-Ph-3-Me-imid)$_3$ is stronger than the N-metal bond in Ir(ppz)$_3$. Moreover, due to the nature of a carbene-metal bond, it is believed that replacing a carbon-metal bond or nitrogen-metal bond in existing emissive organometallic molecules with a carbene-metal bond (making other changes as needed to make the carbon atom a carbene) may result in an emissive molecule that is more stable than the non-carbene analog, and that has stronger spin-orbit coupling. It is further believed that the emissive spectra of the molecule including a carbene may be different from the emissive spectra of the analog without a carbene.

Metal-carbene complexes may be tuned to emit a wide variety of spectra from the near-ultraviolet across the entire visible spectra by the selection of substituents and/or chemical groups on the ligand(s). More significantly, it may now be possible to obtain saturated blue color emissions with peak wavelengths at about 450 nm. Because it is believed to be materially easier to reduce than to increase the triplet energy by tuning an emissive compound, the ability to make stable blue emitters at such high energies would also allow for the possibility of obtaining any color by reducing the energy so as to red-shift the emission.

The appropriate selection of substituents and/or chemical groups attached to carbene ligands may also minimize quantum efficiency losses associated with increasing temperatures. The observable difference in lifetime measurements between emission at room temperature and at low temperatures (e.g. 77 K) is believed to be attributed to non-radiative quenching mechanisms that compete with phosphorescent emission. Such quenching mechanisms are further believed to be thermally activated, and consequently, at cooler temperatures of about 77 K, where energy loss due to quenching is not an issue, quantum efficiency is about 100%. It is believed that appropriate substituents on the carbene ligand, or doping in a more rigid matrix, such as disclosed in Turro, "Modem Molecular Photochemistry", University Science Books (1991), 109-10, may increase quantum efficiency at room temperature and correspondingly show longer lifetimes.

Due to the nature of the carbene-metal bond, the emission of a carbene analog may be substantially different from that of its non-carbene analog, and the emission of the carbene analog may be stable and at a higher energy than previously obtainable with stable non-carbene compounds. It is believed that devices incorporating these materials, and having optimized architecture, will have electroluminescent spectra showing high triplet energies.

In some embodiments, the triplet energy of the carbene complex has a corresponding wavelength in the deep blue or ultraviolet (UV) part of the spectra. In some embodiments, the phosphorescent emissive compound has triplet energy corresponding to a wavelength of less than 450 nm. In preferred embodiments, the triplet energy corresponds to a wavelength of less than 440 nm, and in even more preferred embodiments, it corresponds to a wavelength less than 400 nm, which is believed to be in the UV region of the spectrum, since 400 nm is believed to represent the cut-off between the UV and the visible regions of the spectrum. Such high triplet energy may make these compounds useful in optically pumping down converting layers. For such applications, an overlap is preferred between the emission spectra of the ultraviolet carbene compound and the absorption spectra of the down converting layer. It is believed that when about 50% of the integral of the curve for the normalized electroluminescent spectra of the device is at a wavelength less than about 450 nm, there is sufficient energy to optically pump a down converting layer. More preferably, greater than 90% of the emission may be produced below 440 nm, as disclosed herein. Preferably, 50% of the integral of the curve for the normalized electroluminescent spectra is less than about 440 nm, and more preferably, it is less than about 400 nm. The wavelength cutoffs mentioned above are not intended to be absolute limitations as they depend on the energy of the material to be pumped. It is also believed that these emissions may occur at room temperature.

The strong metal-carbon bond is also believed to lead to greater spin-orbit coupling in metal carbene complexes. Moreover, the triplet energy of coordinated carbenes are shown to be significantly higher than pyridine analogs. The emission is shown to be in the near-ultraviolet range of the spectrum even at room temperature. It is believed herein that other metal carbene complexes may be capable of emitting at similarly high energies due to the strong metal-ligand bond associated with carbene ligands.

The stability of metal-carbene complexes may also allow increased versatility in the types of ligands and metals that may be used as phosphorescent emitters in OLEDs. The strong metal-carbene bond may allow a variety of metals to form useful phosphorescent complexes with carbene ligands to give novel emissive compounds. For example, gold or copper may be bonded to a carbene ligand. Such metals have been calculated to form metal-carbon bonds having quite high bond dissociation energies, such as illustrated in Nemcsok et al., "The Significance of π-Interactions in Group 11 Complexes with N-Heterocyclic Carbenes," American Chemical Society, Publ. on Web, Jun. 19, 2004. Such high bond dissociation energies may be expected to improve the chemical stability of metal-carbene complexes as compared with the analogous metal-phenyl-pyridine ("metal-ppy") based complexes that are typically used in an OLED. Thus, in addition to their use as the emissive materials in an OLED, metal-carbene complexes may be also used advantageously, because of their improved chemical stability, for other functions in an OLED, for example, as a host material in the emissive layer, as an electron or hole transporting material in an electron or hole transporting layer, and/or as an electron or hole blocking material in an electron or hole blocking layer.

It is believed that many of the (C,C) or (C,N) ligands of many existing electroluminescent compounds may be modified to create an analogous (C,C) ligand including a carbene. Specific non limiting examples of such modification include:

(1) the substituents on the carbene-bonded branch of the (C,C)-ligand and the substituents on the mono-anionic-carbon-bonded branch of the (C,C)-ligand may be independently selected from the group consisting of
  (a) the substituents on the N-bonded branch of the existing (C,N)-ligands, such as disclosed in the references listed below, which is typically but not necessarily a pyridine group; and
  (b) the substituents on the mono-anionic-carbon-bonded branch of the existing (C,N)-ligands, such as disclosed in the references listed below, which is typically but not necessarily a phenyl group;
  (c) and/or a combination thereof; and (2) the compounds including the metal-carbene bonds may further include ancillary ligands selected from the group consisting of the ancillary ligands such as disclosed in the following references:

U.S. Pat. Application Publ. No. 2002-0034656, FIGS. 11-50, U.S. Pat. Application Publ. No. 2003-0072964 (Thompson et al.), paragraphs 7-132; and FIGS. 1-8; U.S. Pat. Application Publ. No. 2002-0182441 (Lamansky et al.), paragraphs 13-165, including FIGS. 1-9(g); U.S. Pat. No. 6,420,057 B1 (Ueda et al.), col. 1, line 57, through col. 88, line 17, including each compound I-1 through XXIV-12; U.S. Pat. No. 6,383,666 B1 (Kim et al.), col. 2, line 9, through col. 21, lin367; U.S. Pat. Application Publ. No. 2001-0015432 A1 (Igarashi et al.), paragraphs 2-57, including compounds (1-1) through (1-30); U.S. Pat. Application Publ. No. 2001-0019782 A1 (Igarashi et al.), paragraphs 13-126, including compounds (1-1) through (1-70), and (2-1) through (2-20); U.S. Pat. Application Publ. No. 2002-0024293 (Igarashi et al.), paragraphs 7-95, including general formulas K-I through K-VI, and example compounds (K-1) through (K-25); U.S. Pat. Application Publ. No. 2002-0048689 A1 (Igarashi et al.), paragraphs 5-134, including compounds 1-81, and example compounds (1-1) through (1-81); U.S. Pat. Application Publ. No. 2002-0063516 (Tsuboyama et al.), paragraphs 31-161, including each compound 1-16; U.S. Pat. Application Publ. No. 2003-0068536 (Tsuboyama et al.), paragraphs 31-168, including each compound in Tables 1-17, corresponds to EP-1-239-526-A2; U.S. Pat. Application Publ. No. 2003-0091862 (Tokito et al.), paragraphs 10-190, including each compound in Tables 1-17, corresponds to EP-1-239-526-A2; U.S. Pat. Application Publ. No. 2003-0096138 (Lecloux et al.), paragraphs 8-124, including FIGS. 1-5; U.S. Pat. Application Publ. No. 2002-0190250 (Grushin et al.), paragraphs 9-191; U.S. Pat. Application Publ. No. 2002-0121638 (Grushin et al.), paragraphs 8-125; U.S. Pat. Application Publ. No. 2003-0068526 (Kamatani et al.), paragraphs 33-572, including each compound in Tables 1-23; U.S. Pat. Application Publ. No. 2003-0141809 (Furugori et al.), paragraphs 29-207; U.S. Pat. Application Publ. No. 2003-0162299 A1 (Hsieh et al.), paragraphs 8-42; WO 03/084972, (Stossel et al.), Examples 1-33; WO 02/02714 A2 ((Petrov et al.), pages 2-30, including each compound in Tables 1-5; EP 1-191-613 A1 (Takiguchi et al.), paragraphs 26-87, including each compound in Tables 1-8, (corresponding to U.S. Pat. Application Publ. No. 2002-0064681); and EP 1-191-614 A2 (Tsuboyama et al.), paragraphs 25-86, including each compound in Tables 1-7; which are incorporated herein by reference in their entirety.

Carbene ligands may be synthesized using methods known in the art, such as those disclosed in Cattoën, et al., *J. Am. Chem. Soc.*, 2004, 126; 1342-1343; Chiu-Yuen Wong, et al, *Organometallics* 2004, 23, 2263-2272; Klapars, et al, *J. Am. Chem. Soc.*, 2001, 123; 7727-7729; Bourissou et al. *Chem Rev.* 2000, 100,39-91; Siu-Wai Lai, et al, *Organometallics* 1999, 18,3327-3336; Wen-Mei Xue et al., *Organometallics* 1998, 17, 1622-1630; Wang & Lin, *Organometallics* 1998, 17, 972-975; Cardin, et al., *Chem Rev.* 1972, 5, 545-574; and other references discussed herein.

A process is provided for preparing a compound having the formula L$_2$IrL'. The process comprises:

(a) combining

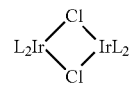

and L' in the presence of an organic solvent to form a mixture;

(b) maintaining the mixture for sufficient time to obtain L$_2$IrL';

(c) recovering L$_2$IrL' from the mixture, and where L is a carbene ligand coordinated to iridium and L' is a bidentate ligand or two monodentate ligands, and L is different from L'. L' may be a carbene or non-carbene ligand. In preferred embodiments, L and L' are both bidentate carbene ligands. In preferred embodiments, L' has a net negative charge and L$_2$IrL' is a neutral compound. In other embodiments, L' is neutral and L$_2$IrL' is positively charged.

Preferably, L has the structure

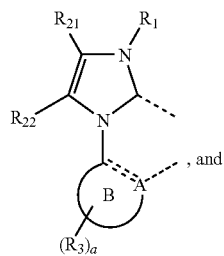

A may be C or N; ring B may be an aromatic cyclic, heterocyclic, fused cyclic, or fused heterocyclic ring, wherein ring B may be optionally substituted with one or more substituents $R_3$; $R_1$ may be hydrogen, alkyl, alkenyl, alkynyl, aralkyl, aryl, heteroaryl, substituted aryl, substituted heteroaryl, or a heterocyclic group; $R_{21}$, $R_{22}$, and $R_3$ may each independently be hydrogen, alkyl, alkenyl, alkynyl, aralkyl, CN, $CF_3$, $CO_2R'$, $C(O)R'$, $C(O)NR'2$, $NR'2$, $NO_2$, $OR'$, $SR'$, $SO_2$, $SOR'$, $SO_3R'$, halo, aryl, heteroaryl, substituted aryl, substituted heteroaryl, or a heterocyclic group; and additionally or alternatively, $R_{21}$ and $R_{22}$, and/or two $R_3$ groups on adjacent ring atoms may form a fused 4-7-membered aromatic group, wherein said aromatic group may be cycloalkyl, cycloheteroalkyl, aryl or heteroaryl; and wherein said aromatic group may be optionally substituted by one or more substituents J; each substituent J may be R', CN, $CF_3$, $C(O)OR'$, $C(O)R'$, $C(O)NR'_2$, $NR'_2$, $NO_2$, $OR'$, $SR'$, $SO_2$, $SOR'$, or $SO_3R'$, and additionally, or alternatively, two J groups on adjacent ring atoms may form a fused 4-7-membered aromatic group; each R' may be halo, H, alkyl, alkenyl, alkynyl, heteroalkyl, aralkyl, aryl and heteroaryl.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, $C(O)R$, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The terms "aralkyl" as used herein contemplates an alkyl group that has as a substituent an aromatic group. Additionally, the aralkyl group may be optionally substituted on the aryl with one or more substituents selected from halo, CN, $CO_2R$, $C(O)R$, $NR_2$, cyclic-amino, $NO_2$, and OR.

The term "heterocyclic group" as used herein contemplates non-aromatic cyclic radicals. Preferred heterocyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like.

The term "aryl" or "aromatic group" as used herein contemplates single-ring groups and polycyclic ring systems. The polycyclic rings may have two or more rings in which two carbons are common by two adjoining rings (the rings are "fused") wherein at least one of the rings is aromatic, e.g., the other rings can be cycloalkyls, cycloalkenyls, aryl, heterocycles and/or heteroaryls.

The term "heteroaryl" as used herein contemplates single-ring hetero-aromatic groups that may include from one to four heteroatoms, for example, pyrrole, furan, thiophene, imidazole, oxazole, thiazole, triazole, tetrazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles and/or heteroaryls.

More preferably, L has the structure:

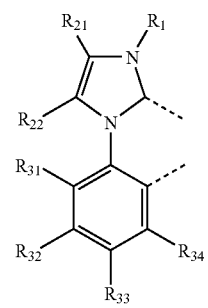

wherein $R_{31}$-$R_{34}$ may each be hydrogen, alkyl, alkenyl, alkynyl, aralkyl, CN, $CF_3$, $CO_2R'$, $C(O)R'$, $C(O)NR'2$, $NR'2$, $NO_2$, $OR'$, $SR'$, $SO_2$, $SOR'$, $SO_3R'$, halo, aryl, heteroaryl, substituted aryl, substituted heteroaryl, or a heterocyclic group; and additionally or alternatively, $R_{21}$ and $R_{22}$, and two $R_3$ groups on adjacent ring atoms may form a fused 4-7-membered aromatic group, wherein said aromatic group may be cycloalkyl, cycloheteroalkyl, aryl or heteroaryl; and wherein said aromatic group may be optionally substituted by one or more substituents J; each substituent may be R', CN, $CF_3$, $C(O)OR'$, $C(O)R'$, $C(O)NR'_2$, $NR'_2$, $NO_2$, $OR'$, $SR'$, $SO_2$, $SOR'$, or $SO_3R'$, and additionally, or alternatively, two J groups on adjacent ring atoms may form a fused 4-7-membered aromatic group; each R' may be halo, H, alkyl, alkenyl, alkynyl, heteroalkyl, aralkyl, aryl and heteroaryl.

Most preferably, L has the structure:

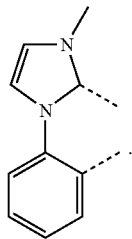

Also provided are heteroleptic compounds, which may be incorporated in OLEDs, having the structure:

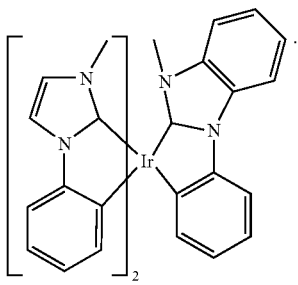

These compounds may be prepared by:
(a) combining

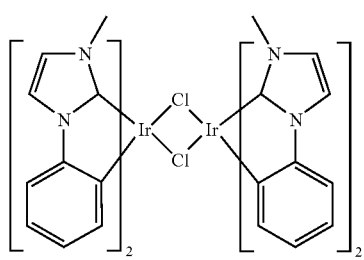

and

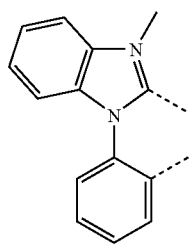

in the presence of an organic solvent to form a mixture;
(b) maintaining the mixture for sufficient time to obtain

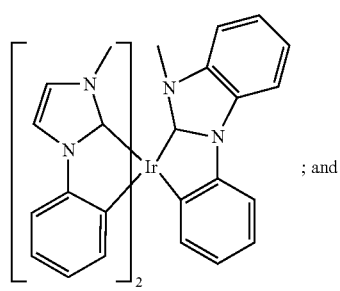

; and (c) recovering

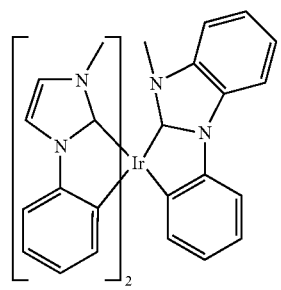

from the mixture.

In addition, a compound with the structure

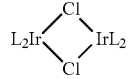

is provided, in which L is a carbene ligand coordinated to iridium. Preferably, L has the structure:

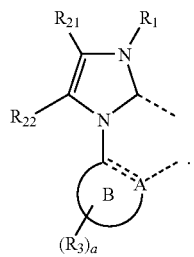

More preferably, L has the structure:

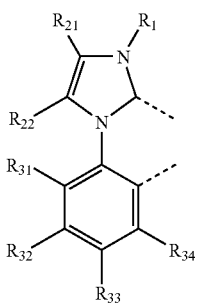

where $R_{31}$-$R_{34}$ may each be hydrogen, alkyl, alkenyl, alkynyl, aralkyl, CN, $CF_3$, $CO_2R'$, $C(O)R'$, $C(O)NR'2$, $NR'2$, $NO_2$, $OR'$, $SR'$, $SO_2$, $SOR'$, $SO_3R'$, halo, aryl, heteroaryl, substituted aryl, substituted heteroaryl, or a heterocyclic group; and additionally or alternatively, $R_{21}$ and $R_{22}$, and two $R_3$ groups on adjacent ring atoms may form a fused 4-7-membered aromatic group, wherein said aromatic group may be cycloalkyl, cycloheteroalkyl, aryl or heteroaryl; and wherein said aromatic group may be optionally substituted by one or more substituents J Most preferably, L has the structure:

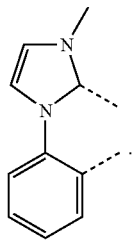

Also provided is a process for the preparing compound having the structure

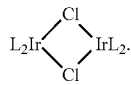

The process includes the step of:
(a) combining L with an organic solvent, wherein L is a suitable carbene ligand precursor;
(b) maintaining the mixture of step (a) at a temperature from about 175° C. to less than the boiling point of the organic solvent to obtain

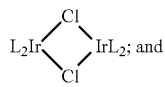

(c) recovering

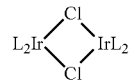

from the mixture. More preferably, the temperature at step (b) is at least about 185° C.

The term "suitable carbene ligand precursor," as used herein, refers to a compound which may generate a free carbene, or a reactive equivalent thereof, under the conditions used to prepare the metal carbene complexes of the present invention. It is known to those skilled in the art that a variety of precursors may be used to generate carbene ligands, including imidazolium salts, silver complexes of carbene ligands, compounds wherein RO—H or Ar—H (where Ar is pentafluorophenyl or similar aryl) are eliminated from the same carbon to generate the carbene, and olefins formally corresponding to the product of carbene-carbene dimerization.

Tris(carbene)iridium complexes have previously been synthesized by reacting a carbene ligand with an organic solvent. These reactions, which are heated to a temperature well below 175° C., are not believed to produce chlorobridged dimers in quantities sufficient to be useful as starting materials for preparing homoleptic or heteroleptic iridium carbene complexes. It has been found that when the above process is heated to temperatures greater than about 175° C. (but below the temperature at which the solvent boils), the reaction becomes unexpectedly selective for chlorobridged dimer complexes. These complexes have also been found to be useful for preparing heteroleptic carbene compounds having the formula $L_2IrL'$, as previously discussed.

Also provided is a process for preparing of a compound with the formula $L_3Ir$, wherein L is a bidentate ligand that may form a five-membered chelate ring. The process comprise:
(a) combining

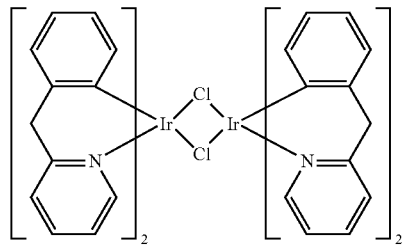

and L in the presence of alcohol and a base to form a mixture;
(b) maintaining the mixture for sufficient time to obtain $L_3Ir$; and
(c) recovering $L_3Ir$ from the mixture.
In preferred embodiments, L has the structure:

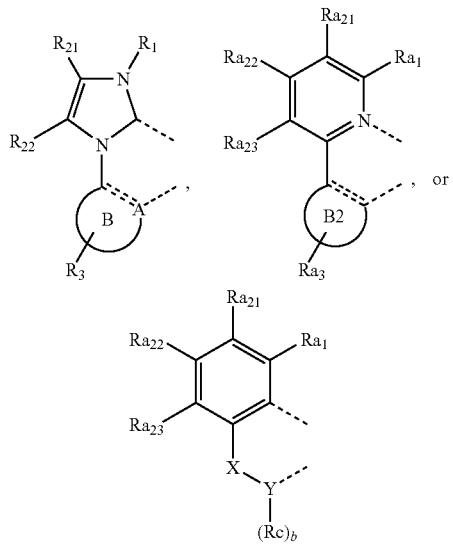

wherein A may be C or N; X may be an alkyl group; Y may be N, P, or C; ring B may be an aromatic cyclic, heterocyclic, fused cyclic, or fused heterocyclic ring, wherein ring B may be optionally substituted with one or more substituents $R_3$; ring B2 may be an aromatic cyclic, heterocyclic, fused cyclic, or fused heterocyclic ring with at least one carbon atom coordinated to metal M, wherein ring B2 may be optionally substituted with one or more substituents $Ra_3$; $R_1$ is independently selected from hydrogen, alkyl, alkenyl, alkynyl, aralkyl, aryl, heteroaryl, substituted aryl, substituted heteroaryl, or a heterocyclic group; $R_{21}$, $R_{22}$, $R_3$, $Ra_1$, $Ra_{21}$, $Ra_{22}$, $Ra_{23}$, and $Ra_3$ are each independently selected from hydrogen, alkyl, alkenyl, alkynyl, aralkyl, CN, $CF_3$, $CO_2R'$, $C(O)R'$, $C(O)NR'2$, $NR'2$, $NO_2$, $OR'$, $SR'$, $SO_2$, $SOR'$, $SO_3R'$, halo, aryl, heteroaryl, substituted aryl, substituted heteroaryl, or a heterocyclic group; and additionally or alternatively, $R_{21}$ and $R_{22}$, two $R_3$ groups, $Ra_1$ and $Ra_{21}$, $Ra_{21}$ and $Ra_{22}$, $Ra_{22}$ and $Ra_{23}$, and two $Ra_3$ groups on adjacent ring atoms may form a fused 4-7-membered aromatic group, which may be cycloalkyl, cycloheteroalkyl, aryl or heteroaryl; and wherein said aromatic group may be optionally substituted by one or more substituents J; each substituent J may be R', CN, CF$_3$, C(O)OR', C(O)R', C(O)NR'$_2$, NR'$_2$, NO$_2$, OR', SR', SO$_2$, SOR', or SO$_3$R', and additionally, or alternatively, two J groups on adjacent ring atoms may form a fused 4-7-membered aromatic group; each may be halo, H, alkyl, alkenyl, alkynyl, heteroalkyl, aralkyl, aryl, and heteroaryl; and b may be 0, 1, or 2.

More preferably, L has the structure:

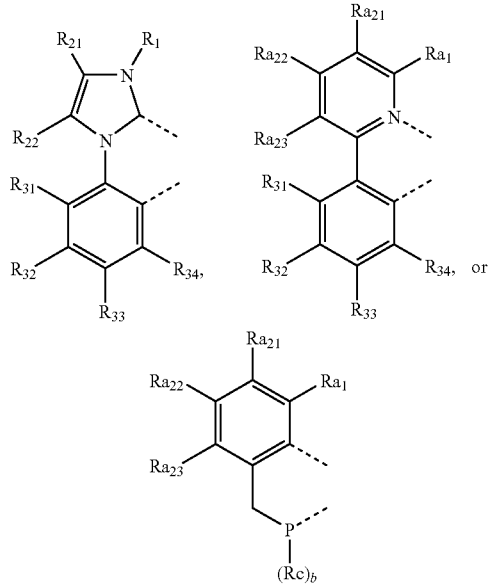

wherein $R_{31}$-$R_{34}$ and $Ra_{31}$-$Ra_{34}$ may each be hydrogen, alkyl, alkenyl, alkynyl, aralkyl, CN, CF$_3$, CO$_2$R', C(O)R', C(O)NR'2, NR'2, NO$_2$, OR', SR', SO$_2$, SOR', SO$_3$R', halo, aryl, heteroaryl, substituted aryl, substituted heteroaryl, or a heterocyclic group; and additionally or alternatively, $R_{21}$ and $R_{22}$, two $R_3$ groups, $Ra_1$ and $Ra_{21}$, $Ra_{21}$ and $Ra_{22}$, $Ra_{22}$ and $Ra_{23}$, and two $Ra_3$ groups on adjacent ring atoms may form a fused 4-7-membered aromatic group, wherein said aromatic group is cycloalkyl, cycloheteroalkyl, aryl or heteroaryl; and wherein said aromatic group may be optionally substituted by one or more substituents J; each substituent J may be independently selected from the group consisting of R', CN, CF$_3$, C(O)OR', C(O)R', C(O)NR'$_2$, NR'$_2$, NO$_2$, OR', SR', SO$_2$, SOR', or SO$_3$R', and additionally, or alternatively, two J groups on adjacent ring atoms may form a fused 4-7-membered aromatic group; each R' may be halo, H, alkyl, alkenyl, alkynyl, heteroalkyl, aralkyl, aryl and heteroaryl.

Most preferably, L has the structure:

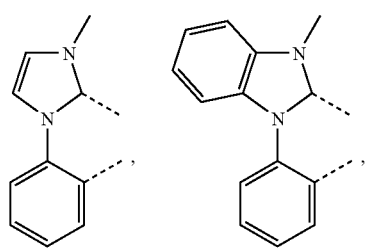

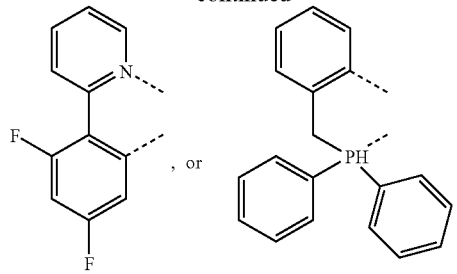

In addition, compounds prepared by the above process are provided. These compounds may also be incorporated into OLEDs. Preferably these compounds have the structure:

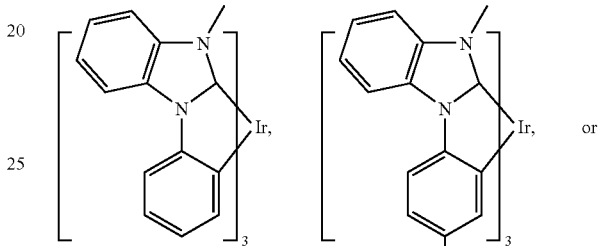

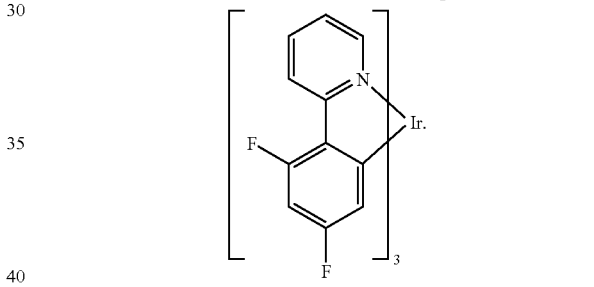

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:

| | |
|---|---|
| CBP: | 4,4'-N,N-dicarbazole-biphenyl |
| m-MTDATA | 4,4',4"-tris(3-methylphenylphenlyamino)triphenylamine |
| Alq$_3$: | 8-tris-hydroxyquinoline aluminum |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F$_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |

-continued

| | |
|---|---|
| ITO: | indium tin oxide |
| NPD: | N,N'-diphenyl-N-N'-di(1-naphthyl)-benzidine |
| TPD: | N,N'-diphenyl-N-N'-di(3-toly)-benzidine |
| BAlq: | aluminum(III)bis(2-methyl-8-hydroxyquinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT: PSS: | an aqueous dispersion of poly(3,4-ethylene-dioxythiophene) with polystyrenesulfonate (PSS) |

Experimental:

Specific representative embodiments of the invention will now be described, including how such embodiments may be made. It is understood that the specific methods, materials, conditions, process parameters, apparatus and the like do not necessarily limit the scope of the invention.

EXAMPLE 1

Synthesis of fac-iridium(III) tris (1-(2-naphthyl-3-methyl-benzimidazoline-2-ylidene-C,$C^2$) and mer-iridium(III) tris (1-(2-naphthyl-3-methyl-benzimidazoline-2-ylidene-C,$C^2$)

A 3 L round-bottomed flask was charged with 113.83 g of silver(I) oxide, 38 g of 1-(2-naphthyl)-3-methyl-benzimidazolate iodide, 9.1 g of iridium trichloride hydrate, and 2000 mL of 2-ethoxyethanol. The reaction was stirred and heated at 120° C. for 2 hours under nitrogen while protected from light with aluminum foil. The reaction mixture was cooled to ambient temperature and concentrated under reduced pressure(20 mmHg). Filtration through Celite using dichloromethane as the eluent was performed to remove the silver(I) salts. A light brown solution was obtained and further purified by flash column chromatography on silica gel using dichloromethane as the eluent yielding 6 g (25.2%) of fac-iridium (III) tris (1-(2-naphthyl-3-methyl-benzimidazoline-2-ylidene-C,$C^2$). The mer isomer was selectively crystallized from a mixture of dichloromethane and methanol. The mother liquid was evaporated to dryness and the residue was recrystallized from dichloromethane to obtain the fac isomer.

EXAMPLE 2

Synthesis of Iridium (III) bis(1-phenyl-3-methyl-imidazoline-2-ylidene-C,$C^2$) chloride dimer A 2 L round-bottomed flask was charged with 80.87 g of silver(I) oxide, 10 g of 1-phenyl-3-methyl-imidazolate iodide and 1 L of dichloromethane. The reaction was stirred at room temperature for 15 h under nitrogen while protected from light with aluminum foil. The reaction mixture was concentrated under reduced pressure. Filtration through Celite using dichloromethane as the eluent was performed to remove the silver(I) salts. The filtrate was concentrated to dryness and transferred to a 2 L round-bottomed flask by re-dissolving it in 2-(2-methoxyethoxy)ethanol (1000 mL). The reaction was stirred and heated to 185° C. under nitrogen. Iridium(III) trichloride hydrate (6.47 g) was added to the reaction mixture while the reaction temperature was maintained at 185° C. The reaction mixture was stirred and heated for a further 5 hours at 185° C. The reaction mixture was cooled to ambient temperature. Filtration through Celite using dichloromethane as the eluent was performed to remove the silver(I) salts. The solvent was removed under reduced pressure. The residue was purified by flash column chromatography on silica gel (30% ethyl acetate in dichloromethane) yielding 2.72 g (28.7%) of Iridium (III) bis(1-phenyl-3-methyl-imidazoline-2-ylidene-C,$C^2$) chloride dimer.

EXAMPLE 3

Synthesis of fac-iridium(III) tris (1-phenyl-3-methyl-benzimidazoline2-ylidene-C,$C^2$)

A 100 mL round-bottomed flask was charged with 740 mg of 1-phenyl-3-methyl-benzimidazoline iodide, 500 mg of Iridium(III) benzylpyridine dichloro bridged dimer, 470 mg of sodium carbonate and 100 mL of 2-ethoxyethanol. The reaction was stirred and heated at 135° C. for 3 h under nitrogen while protected from light with aluminum foil. The reaction mixture was cooled to ambient temperature and concentrated under reduced pressure(20 mmHg). A light brown solution was obtained and further purified by flash column chromatography on silica gel using dichloromethane as the eluent yielding 540 mg (75%) of fac-iridium(III) tris(1-phenyl-3-methyl-benzimidazoline-2-ylidene-C,$C^2$).

EXAMPLE 4

Synthesis of fac-iridium(iii) tris (1-(4-fluorophenyl)-3-methyl-benzimidazoline-2-ylidene-C,$C^2$)

A 100 mL round-bottomed flask was charged with 1.07 g of 1-(4-fluorophenyl)-3-methyl-benzimidazoline iodide, 500 mg of Iridium(III) benzylpyridine dichloro bridged dimer, 470 mg of sodium carbonate and 100 mL of 2-ethoxyethanol. The reaction was stirred and heated at 135° C. for 3 h under nitrogen while protected from light with aluminum foil. The reaction mixture was cooled to ambient temperature and concentrated under reduced pressure(20 mmHg). A light brown solution was obtained and further purified by flash column chromatography on silica gel using dichloromethane as the eluent yielding 500 mg (65%) of fac-iridium(III) tris (1-(4-fluorophenyl)-3-methyl-benzimidazoline-2-ylidene-C,$C^2$). The pure fac isomer was obtained by recrystallization from methylene chloride.

EXAMPLE 5

Synthesis of mer-tris(2-(4,6-difluoro-phenyl)pyridine)iridium (III)

A 100 mL round-bottomed flask was charged with 1 g of 2-(4,6-difluoro-phenyl)pyridine, 1 g of Iridium(III) benzylpyridine dichloro bridged dimer, 1.128 g of sodium carbonate and 100 mL of 2-ethoxyethanol. The reaction was stirred and heated at 135° C. for 3 h under nitrogen while protected from light with aluminum foil. The reaction mixture was cooled to ambient temperature and concentrated under reduced pressure(20 mmHg). A light brown solution was obtained and further purified by flash column chromatography on silica gel using dichloromethane as the eluent yielding 1 g (74%) of pure mer-tris(2-(4,6-difluoro-phenyl)pyridine)iridium (III).

EXAMPLE 6

Synthesis of mer-iridum(iii) tris(diphenylbenzylphosphine)

A 100 mL round-bottomed flask was charged with 2.4 g of benzyl diphenyl phosphine, 1.4 g of benzylpyridine iridium (III) dichloro bridge dimer, 1.83 g of sodium carbonate and 100 mL of 2-ethoxyethanol. The reaction was stirred and heated at 135° C. for 6 h under nitrogen while protected from light with aluminum foil. The reaction mixture was cooled to ambient temperature and concentrated under reduced pressure(20 mmHg). A light brown solution was obtained and further purified by flash column chromatography on silica gel using dichloromethane and hexanes mixture as the eluent yielding 2 g (78%) of pure mer isomer was obtained.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. A process for preparing a compound having the formula $L_2IrL'$ comprising:
   (a) combining

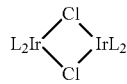

and L' in the presence of an organic solvent to form a mixture,
wherein L is a carbene ligand coordinated to Ir; and L' is a bidentate ligand or two monodentate ligands, and L is different from L';
   (b) maintaining the mixture for sufficient time to obtain $L_2IrL'$;
   (c) recovering $L_2IrL'$ from the mixture.

2. The process of claim 1, wherein L has the structure

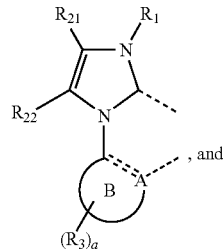

, and

A is independently C or N; ring B is independently an aromatic cyclic, heterocyclic, fused cyclic, or fused heterocyclic ring, wherein ring B can be optionally substituted with one or more substituents $R_3$;

$R_1$ is independently selected from hydrogen, alkyl, alkenyl, alkynyl, aralkyl, aryl, heteroaryl, substituted aryl, substituted heteroaryl, or a heterocyclic group; $R_{21}$, $R_{22}$, and $R_3$ are independently selected from hydrogen, alkyl, alkenyl, alkynyl, aralkyl, CN, $CF_3$, $CO_2R'$, $C(O)R'$, $C(O)NR'2$, $NR'2$, $NO_2$, $OR'$, $SR'$, $SO_2$, $SOR'$, $SO_3R'$, halo, aryl, heteroaryl, substituted aryl, substituted heteroaryl, or a heterocyclic group; and additionally or alternatively, $R_{21}$ and $R_{22}$, and/or two $R_3$ groups on adjacent ring atoms form a fused 4-7-membered aromatic group, wherein said aromatic group is cycloalkyl, cycloheteroalkyl, aryl or heteroaryl; and wherein said aromatic group is optionally substituted by one or more substituents J;

each substituent J is independently selected from the group consisting of R', CN, $CF_3$, $C(O)OR'$, $C(O)R'$, $C(O)NR'_2$, $NR'_2$, $NO_2$, $OR'$, $SR'$, $SO_2$, $SOR'$, or $SO_3R'$, and additionally, or alternatively, two J groups on adjacent ring atoms form a fused 4-7-membered aromatic group; each R' is independently selected from halo, H, alkyl, alkenyl, alkynyl, heteroalkyl, aralkyl, aryl, and heteroaryl;

a is 0, 1, 2, 3, or 4.

3. The process of claim 2, wherein L has the structure:

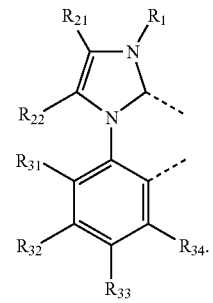

4. The process of claim 3, wherein L has the structure:

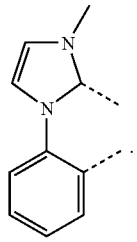

* * * * *

UNITED STATES PATENT AND TRADEMARK OFFICE
CERTIFICATE OF CORRECTION

PATENT NO. : 7,598,388 B2 Page 1 of 1
APPLICATION NO. : 11/032739
DATED : October 6, 2009
INVENTOR(S) : Tsai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1260 days.

Signed and Sealed this

Twenty-eighth Day of September, 2010

David J. Kappos
*Director of the United States Patent and Trademark Office*